(12) United States Patent
Kapke

(10) Patent No.: US 7,454,294 B2
(45) Date of Patent: Nov. 18, 2008

(54) MONITORING Z-VALUES FOR CLINICAL DATA INTERPRETATION

(76) Inventor: Gordon F. Kapke, 812 Franklin Trace, Zionsville, IN (US) 46077

( * ) Notice: Subject to any disclaimer, the term of this patent is extended or adjusted under 35 U.S.C. 154(b) by 0 days.

(21) Appl. No.: 11/653,007

(22) Filed: Jan. 12, 2007

(65) Prior Publication Data

US 2008/0172182 A1     Jul. 17, 2008

(51) Int. Cl.
*G01N 33/50*     (2006.01)
(52) U.S. Cl. .......................................... 702/19
(58) Field of Classification Search ........................ None
See application file for complete search history.

(56) References Cited

U.S. PATENT DOCUMENTS

2005/0013820 A1 *   1/2005  Holoshitz et al. ......... 424/178.1

2008/0026485 A1 *   1/2008  Hueber et al. ............... 436/507

* cited by examiner

*Primary Examiner*—Bryan Bui
*Assistant Examiner*—Jonathan Teixeira Moffat
(74) *Attorney, Agent, or Firm*—McDermott Will & Emery LLP

(57) ABSTRACT

Clinical data that are measured at a plurality of sequential time points are interpreted by monitoring the Z-value of the clinical data. The Z-value of the measured data is calculated at each of the time points. The calculated Z-values are plotted and compared against a pre-selected Z-value, which may be Z=5, in one exemplary embodiment. The clinical data are determined to have undergone a statistically significant change, compared to a baseline value BV of the data, when the calculated Z-value for the measured data is greater than or substantially equal to the pre-selected Z-value. In this way, signal detection from biomarker data may be enhanced. Also, the toxicity level of drugs that are tested in clinical trials may be determined in a more reliable fashion.

18 Claims, 16 Drawing Sheets

ALT ALERT SIGNAL DETECTION

| CRITERIA | DATA MEETING CRITERIA |
|---|---|
| >2 x ULN | 12 |
| >2 x ULN; Z>5 | 12 |
| <2 x ULN; Z>5 ($CV_A$ =6%, $CV_I$ = 24%) | 25 |
| <2 x ULN; Z>5 ($CV_A$ =3%, $CV_I$ = 24%) | 26 |
| <2 x ULN; Z>5 ($CV_A$ =6%, $CV_I$ = 16%) | 52 |
| <2 x ULN; Z>5 ($CV_A$ =3%, $CV_I$ = 16%) | 57 |

ULN = UPPER LIMIT OF NORMAL
ALT REFERENCE INTERVAL IS 6-43 U/L
$C_A$ = ANALYTICAL PRECISION (%)
$C_I$ = INTRA-INDIVIDUAL BIOLOGICAL VARIATION (%)

FIG. 2E

AST ALERT SIGNAL DETECTION

| CRITERIA | DATA MEETING CRITERIA |
|---|---|
| >2 x ULN | 0 |
| <2 x ULN; Z>5 ($C_A$ =5%, $C_I$ = 12%) | 19 |
| <2 x ULN; Z>5 ($C_A$ =5%, $C_I$ = 8%) | 28 |

ULN = UPPER LIMIT OF NORMAL
AST REFERENCE INTERVAL IS 11-36 U/L
$CV_A$ = ANALYTICAL PRECISION (%)
$CV_I$ = INTRA-INDIVIDUAL BIOLOGICAL VARIATION (%)

FIG. 3C

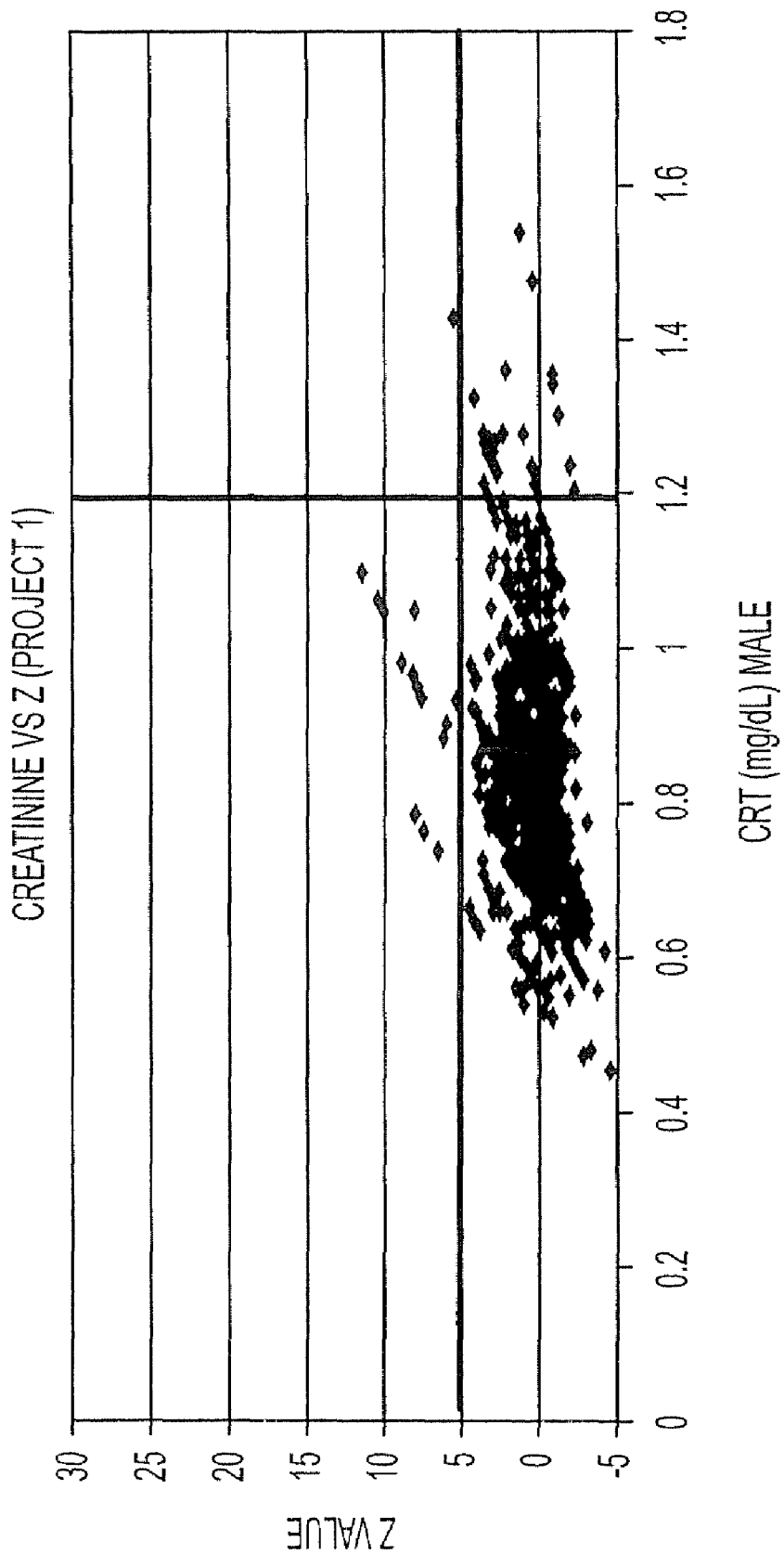

CREATININE: Z VS FIXED LIMITS FOR SIGNAL IDENTIFICATION

GRADE 1 TOXICITY                          1.1-1.5 ULN
ADULT MALE REFERENCE INTERVAL     0.5-1.2 mg/dL

| BASELINE mg/dL | VISIT mg/dL | Z | TOXICITY GRADE |
|---|---|---|---|
| 0.6 | 1.32 | 17.0 | 1 |
| 0.8 | 1.32 | 9.2 | 1 |
| 1.0 | 1.32 | 4.5 | 1 |
| 1.2 | 1.32 | 1.4 | 1 |
| 0.6 | 1.80 | 28.3 | 1 |
| 0.8 | 1.80 | 17.7 | 1 |
| 1.0 | 1.80 | 11.3 | 1 |
| 1.2 | 1.80 | 7.1 | 1 |

FIG. 7

MONITORING Z-VALUES FOR CLINICAL DATA INTERPRETATION

BACKGROUND

The significance of changes in serial test results must be properly assessed, for example during clinical trials which tend to be time consuming and expensive. Because of weak signals from biomarker data, critical data obtained during phase I clinical trials can be difficult to interpret. Accurate interpretation of these signals is of great interest, because significant resources are often spent on compounds that ultimately fail in phase III clinical trials.

There is a need for methods and systems that allow clinical laboratory data to be quantitated more effectively and reliably.

SUMMARY

A method is described for interpreting clinical data that are measured at a plurality of sequential time points. The method includes monitoring the Z-value of the data by calculating for each time point a Z-value of the data measured at that time point, and comparing the calculated Z-value against a pre-selected Z-value. The method further includes identifying a statistically significant change in the clinical data as compared to a baseline value BV, when the calculated Z-value is greater than, or substantially equal to, the pre-selected Z-value.

An apparatus for interpreting clinical data measured at a plurality of time points may include a processing system configured to monitor the Z-value of the clinical data by calculating at each time point the Z-value for the data measured at that time point and comparing the calculated Z-value against a pre-selected Z-value. The processing system is further configured to identify a statistically significant change in the clinical data compared to a baseline value BV of the data, when the calculated Z-value is greater than, or substantially equal to, the pre-selected Z-value.

BRIEF DESCRIPTION OF THE DRAWINGS

FIG. 2E is a table that summarizes the data in FIGS. 2A-2D to illustrate alert signal detection for ALT.

FIG. 3C is a table that summarizes the data shown in FIGS. 3A-3B, to illustrate alert signal detection for AST.

FIG. 5A illustrates a plot of Z-values of the concentration of Creatinine measured for a population of individuals during a Phase II stage of a clinical trial.

FIG. 7 tabulates the calculated Z-values versus traditional fixed limits, for signal identification in the Creatinine data.

DETAILED DESCRIPTION

In the present disclosure, methods and systems are described in which the significance of changes in serial measurements of clinical data is assessed by calculating and monitoring the Z-values of the clinical data. In particular, clinical events are reviewed based on Z-values calculated from the analytical precision, the intra-individual biological variability, and the reference change value.

A number of methods have been used to statistically analyze serial measurements of clinical data, and specifically in order to determine the significance of an observed change between consecutive measurements. One method included measuring the test results against different types of clinical fixed limits or cut-off criteria. Using this method, the medical practitioner determined that a statistically significant change in the serial measurements has occurred, if the measured value of the clinical data rises to a level above the clinical fixed limit or cut-off criterion that was selected for that particular study. The statistically significant change provides an alert for the occurrence of a clinically significant event, such as the reaching of toxic level by the drug, in which case the medical practitioner would determine that drug treatment should be discontinued.

The above-described cut-off criteria or signal detection limits have typically been defined as a multiple of an upper limit of a reference interval, e.g. an upper level of normal (ULN). The ULN for some analytes (such as enzymes) may, however, vary by more than 50% across laboratories that use the same method. With such a variation in the definition of normal, the question arises as to how critical phase I clinical laboratory data should be interpreted. This question is of particular concern because significant resources tend to be spent on compounds that ultimately fail in phase III clinical trials, and therefore improving signal detection from biomarker data is of great interest.

The present disclosure describes how signals can be more effectively quantitated in clinical laboratory data by evaluating the Z-statistic or Z-value from the serial measurements. FIGS. 1, 2A-2D, and 3A-3B illustrate this technique as applied to an evaluation of historical phase I data for ALT and AST. The measurements were performed for a population of adult males during a series of clinical visits made over a period of one month.

Figure 1:
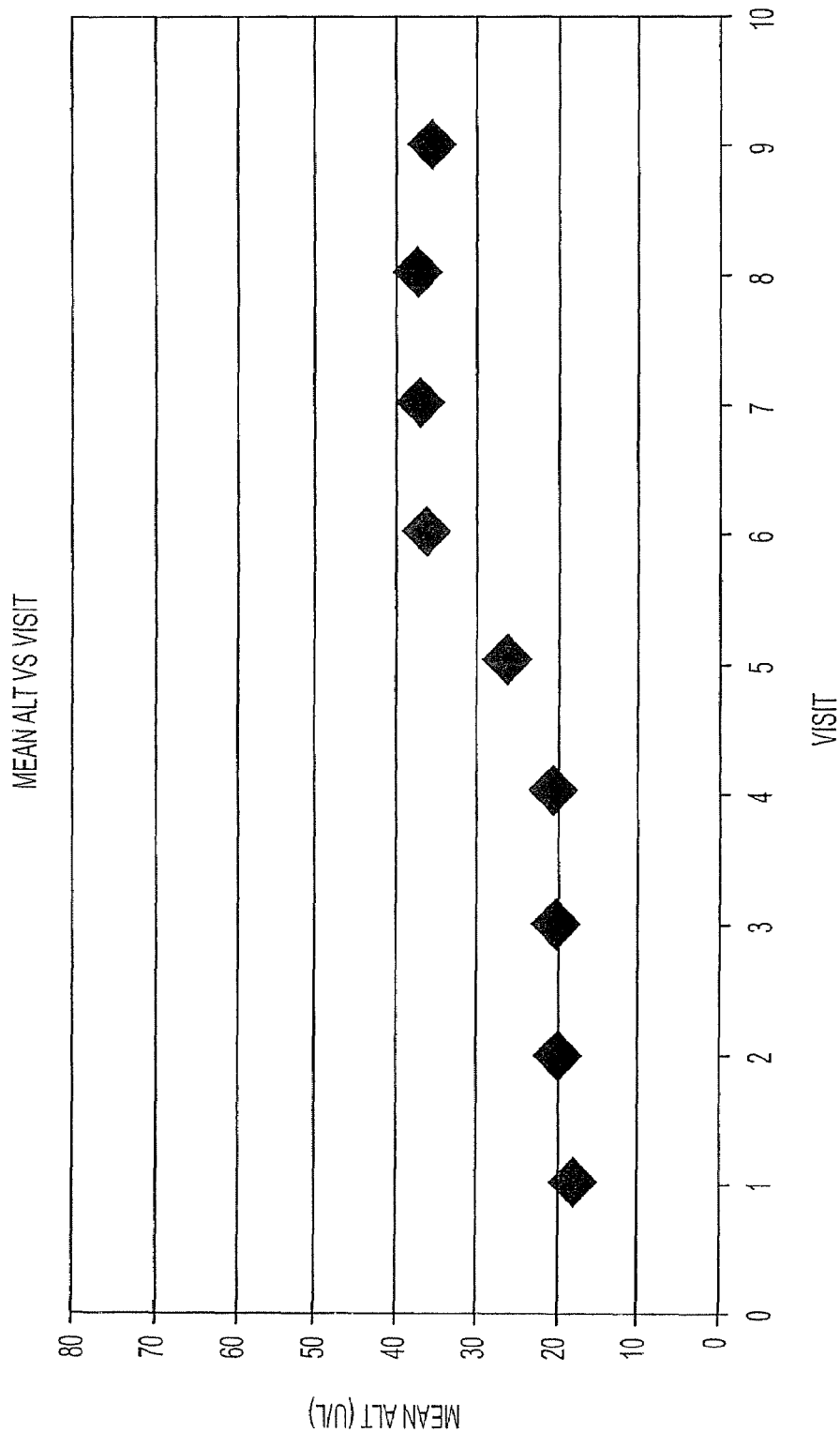
FIG. 1 is a graph of the mean value of the concentration of ALT (Alanine Aminotransferase), as measured serially during a Phase I stage of a clinical trial.

FIG. 1 is a graph of the mean value of the concentration of ALT (Alanine Aminotransferase), as measured serially during a Phase I stage of a clinical trial, as a function of the individual visits. ALT is a type of a biomarker, and can be used to detect liver damage. Biomarkers are parameters associated with the presence and severity of particular disease states, and are helpful when evaluating the safety or effectiveness of drugs. The biomarker ALT, in particular, can be used in conjunction with clinical trials or administrations of a drug for which liver function tests are recommended to indicate the occurrence of drug-induced liver damage.

FIG. 1 shows that the ALT results increase, during the one month period of time in which the study is conducted. FIG. 1 shows, however, that the mean ALT results remain within the reference interval, which for ALT happens to be 6-43 U/L. The question remains, therefore, as to how one should interpret the safety of the drug being tested from the phase I data.

FIGS. 2A-2D are graphs of the Z-values of the concentration of ALT, calculated for analytical precisions of 3% and 6% and biological variation of 24% and 16%, respectively, plotted against the measured ALT concentration. The vertical dotted line in all of the figures (FIG. 2A, 2B, 2C, and 2D) indicates a measured concentration value of two times the upper limit of normal.

As known, the Z-value (also referred to as Z-score, Z-statistic, or standard normal deviate) of an item indicates how much the item deviates from its distribution's mean, expressed in terms of its distribution's standard deviation. The Z-values shown in FIGS. 2A-2D are calculated from the analytical precision ($CV_A$), the intra-individual biological variability ($CV_I$), and the reference change value (RCV), as explained below.

When interpreting clinical data, biological variation must be taken into account. In other words, the fact that many analytes of interest can vary over an individual's lifetime, because of natural biological factors, must be taken into account. It is known that a series of samples from a particular individual for a particular laboratory test may not yield exactly the sample results, because test results for any individual generally vary over time. It is also known that such a variation includes the following: 1) pre-analytical variation $CV_P$; 2) analytical variation $CV_A$; and 3) intra-individual biological variation $CV_I$.

The pre-analytical variation $CV_P$ results from pre-analytical influences, which are influences that results from factors such as the preparation of the individual for sampling, and from sample collection. The analytical variation $CV_P$ results from analytical random error, i.e. precision, and sometimes also from systematic error such as changes in bias due to calibration. The intra-individual biological variation $CV_I$, also referred to as within-subject biological variation, refers to the inherent biological variation around the homeostatic setting point of an individual subject.

The pre-analytical variation $CV_P$, the analytical variation $CV_A$, and the within-subject biological variation $CV_I$ are all random, and can be considered Gaussian. In order to be confident that the results of serial measurements perform for an individual have undergone a clinically significant change, the difference in successive results must exceed that which can be explained by the inherent variation due to the above three components.

The total result variation $CV_T$ can be defined in terms of the pre-analytical variation $CV_P$, the analytical variation $CV_A$, and intra-individual biological Variation $CV_I$ as follows:

$$CV_T = (CV_P^2 + CV_A^2 + CV_I^2)^{0.5} \quad \text{Eq. (1)}$$

If the pre-analytical variation $CV_P$ is very small because sample collection is well controlled, then the total result variation $CV_T$ can be defined, to a good approximation, as follows:

$$CV_T = (CV_A^2 + CV_I^2)^{0.5} \quad \text{Eq. (2)}$$

Assuming that the variations are gaussianly distributed, statistically the following occurs:

Measured Value±1 $CV_T$ occurs at a frequency of 68.3%;

Measured Value±2 $CV_T$ occurs at a frequency of 95.5%;

Measured Value±3 $CV_T$ occurs at a frequency of 99.7%. Eq. (3)

This is because, in any Gaussian distribution, about 0.3415 of the total area under the Gaussian distribution curve lies between the mean and Z=1.

In Eq. (3) above, the multipliers 1, 2, and 3 are called standard normal deviates, or Z-values. For a given laboratory measurement, the value of the laboratory measurement lies within the range $\pm Z^* CV_T$ or $\pm Z^*(CV_A^2 + CV_I^2)^{0.5}$, with a probability associated with the Z-value.

The expected total variation for two separately collected samples can be determined as set forth below. For two laboratory values, respectively collected during two separate tests (Test 1 and Test 2), each value has a probability distribution of $Z^*(CV_A^2 + CV_I^2)^{0.5}$, as explained above. The total variation is given by:

$$\text{Total variation} = [(\text{variation Test 1})^2 + (\text{variation of Test 2})^2]^{0.5} \quad \text{Eq. (4)}$$

Using Eq. (2), the total variation is given by:

$$\text{Total variation} = \{[Z^*(CV_A^2 + CV_I^2)^{0.5}]^2 + [Z^*(CV_A^2 + CV_I^2)^{0.5}]^2\}^{0.5} \quad \text{Eq. (5)}$$

It is known to statistically calculate a reference change value (RCV), in order to assess the significance of the observed change between two successive measurements. The reference change value (RCV) is defined as that difference between two test results in an individual that is statistically significant in a given proportion of a population of similar individuals. The reference change value must be selected as that difference between values that would be statistically significant in a large majority of the individuals concerned.

The total variation defined in terms of the analytical variation $CV_A$ and the within-subject biological variation $CV_I$ can be selected as the reference change value RCV. In this case, using Eq. (4) and Eq. (5) above, the reference change value RCV is thus given by:

$$RCV = 2^{0.5} * Z^*(CV_A^2 + CV_I^2)^{0.5} \quad \text{Eq. (6)}$$

From Eq. (6), the Z-value is given by:

$$Z = RCV/[2^{0.5} * (CV_A^2 + CV_I^2)^{0.5}] \quad \text{Eq. (7)}$$

In equations (6) and (7) above, RCV, $CV_A$, and $CV_I$ are in units of percent.

As explained in Eq. (3) above, the value of a laboratory measurement lies within the range $\pm Z^* CV_T$ with a probability associated with the Z value. For example, the probability of 95.5% is associated with a Z-value of 2. A Z-value of 1.96, with which a probability of 95% is associated, is typically viewed as indicating the occurrence of a significant change the data. A Z-value of 2.58, with which a probability of 99% is associated, is typically viewed as indicating the occurrence of a highly significant change the data.

In FIGS. 2A-2D, ALT data were analyzed from a historical Phase I study by calculating the Z-value, i.e. the probability of change, using baseline and subsequent visits. The Z-values shown in FIGS. 2A-2D have been plotted as a function of a series of visits against the ALT concentration measured at each visit. The Z-value at each of the plurality of visits were calculated in terms of the analytical precision $CV_A$, the intra-individual biological variability $CV_I$, and the reference change value RCV, where the reference change value RCV for a particular visit is given in terms the difference between a baseline value BV and a visit value V which is the value as measured during that particular visit:

$$Z = [100 \times (\text{baseline } BV - \text{visit } V)/\text{baseline } BV] / \quad \text{Eq. (8)}$$
$$[2^{0.5} * (CV_A^2 + CV_I^2)^{0.5}]$$
$$= \text{percentage change} / [2^{0.5} * (CV_A^2 + CV_I^2)^{0.5}]$$
$$= (RCV \text{ as a percentage}) / [2^{0.5} * (CV_A^2 + CV_I^2)^{0.5}]$$

As explained above, a Z value of 2.58 represents a 99% probability of a true change in analyte concentration. To filter noise, a Z value of >5 was arbitrarily chosen as a criteria for signal detection for the ALT data.

The ALT data was generated from a population of adult males over one month. Analytical precision was estimated from quality control data. Intra-individual biological variation was obtained from the Biological Variation Database. The Biological Variation Database and NHANES data generate very similar estimates of intra-individual biological variation. For ALT, this was 24.3% vs. 23.7%.

Figure 2A:
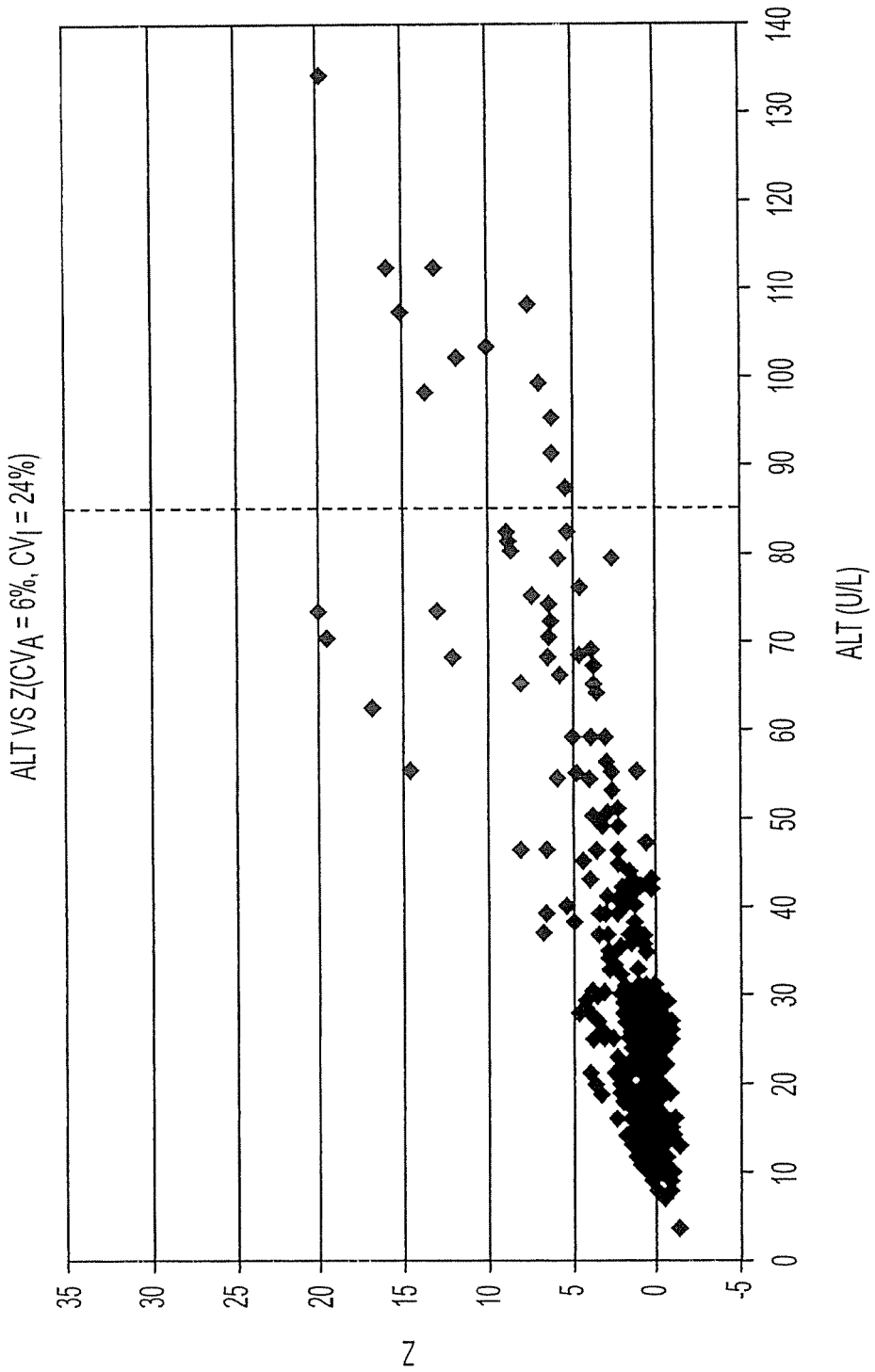
FIGS. 2A-2D are graphs of the Z-values of the concentration of ALT, calculated for analytical precisions of 3% and 6% and biological variations of 24% and 16% respectively, plotted against the ALT concentration.
Figure 2B:
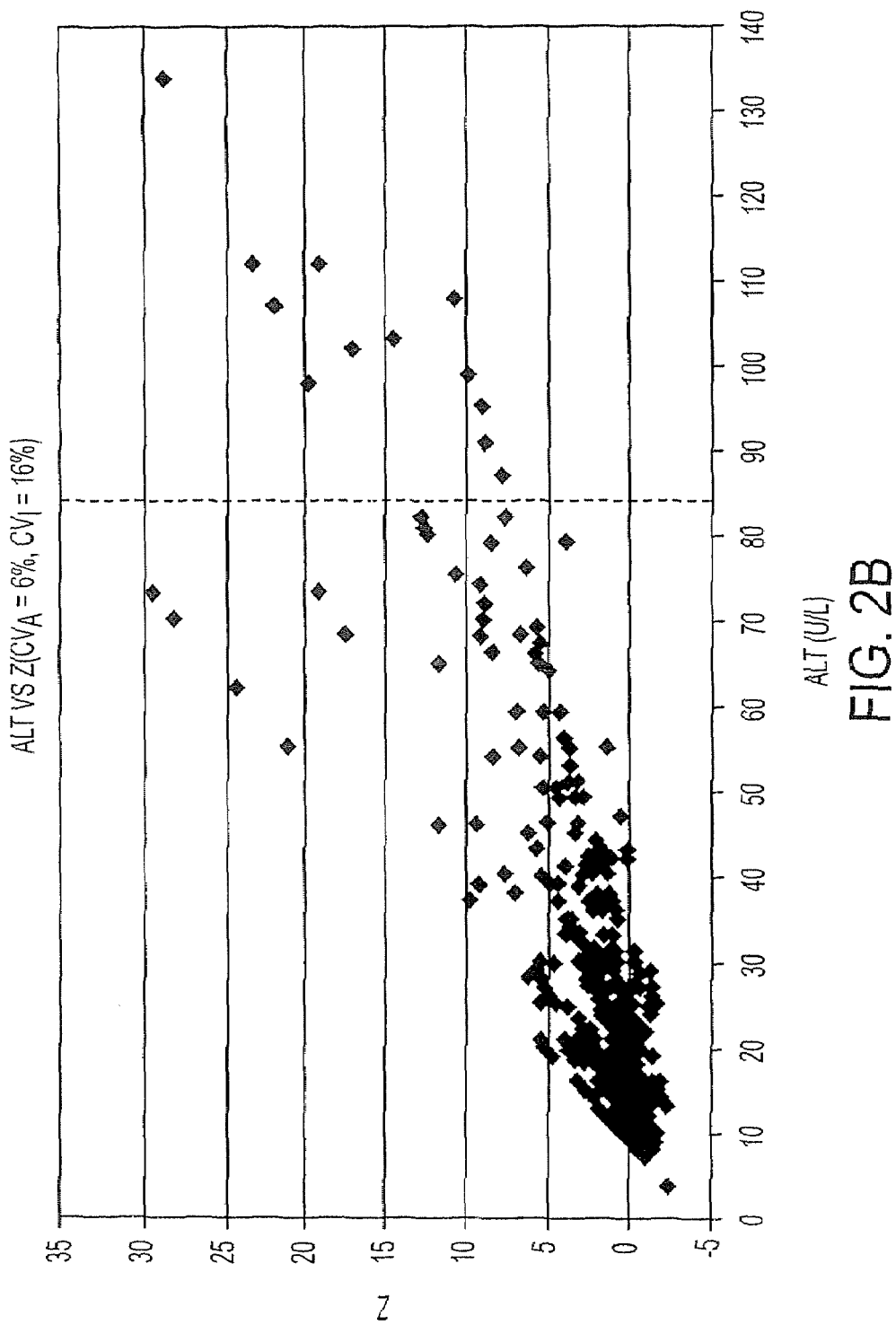
Figure 2C:
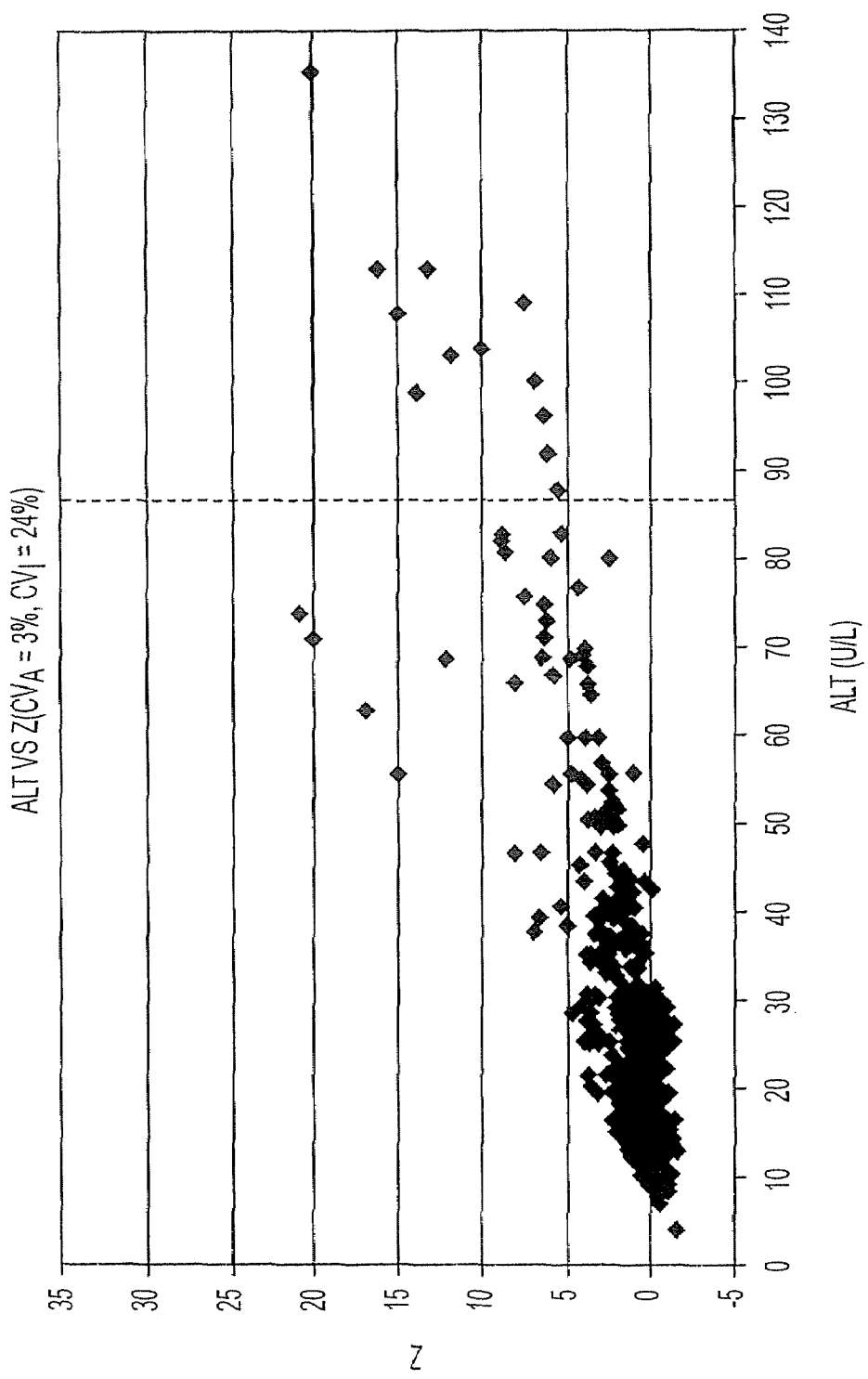
Figure 2D:
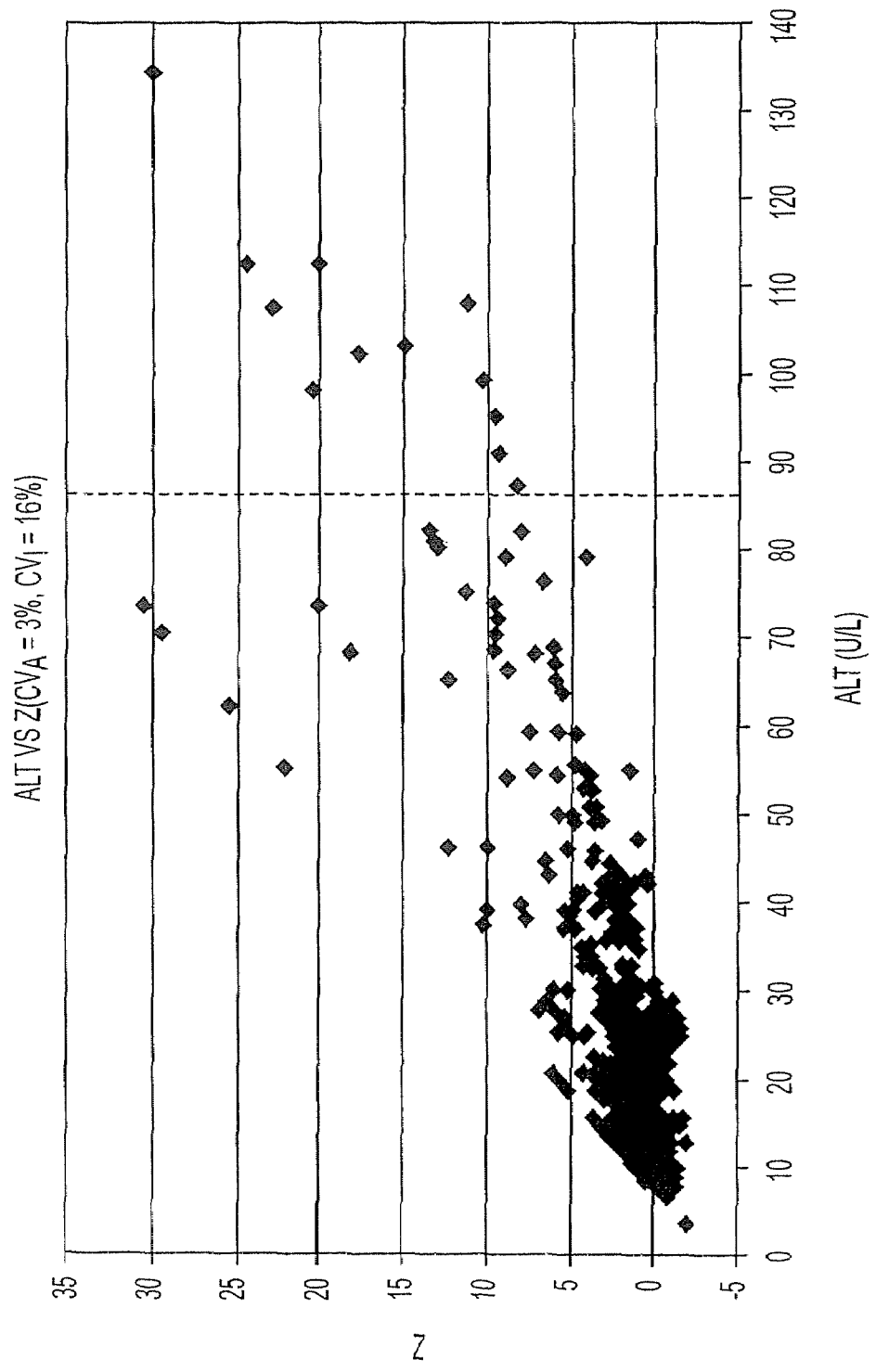

FIG. 2E is a table that summarizes the data in FIGS. 2A-2D to illustrate alert signal detection for ALT. As explained above, Z values have been calculated for analytical precision of 3% and 6% with a biological variation of 24% and 16%, to account for patient auto-correlation over short time intervals. As seen from FIG. 2E, all ALT results exceeding 2×ULN had Z values greater than 5. Substantially more Z values greater than 5 were observed at ALT results less than 2× ULN, as compared to ALT results greater than 2× ULN, where 2×ULN is illustrated by the dashed vertical line.

Figure 3A:
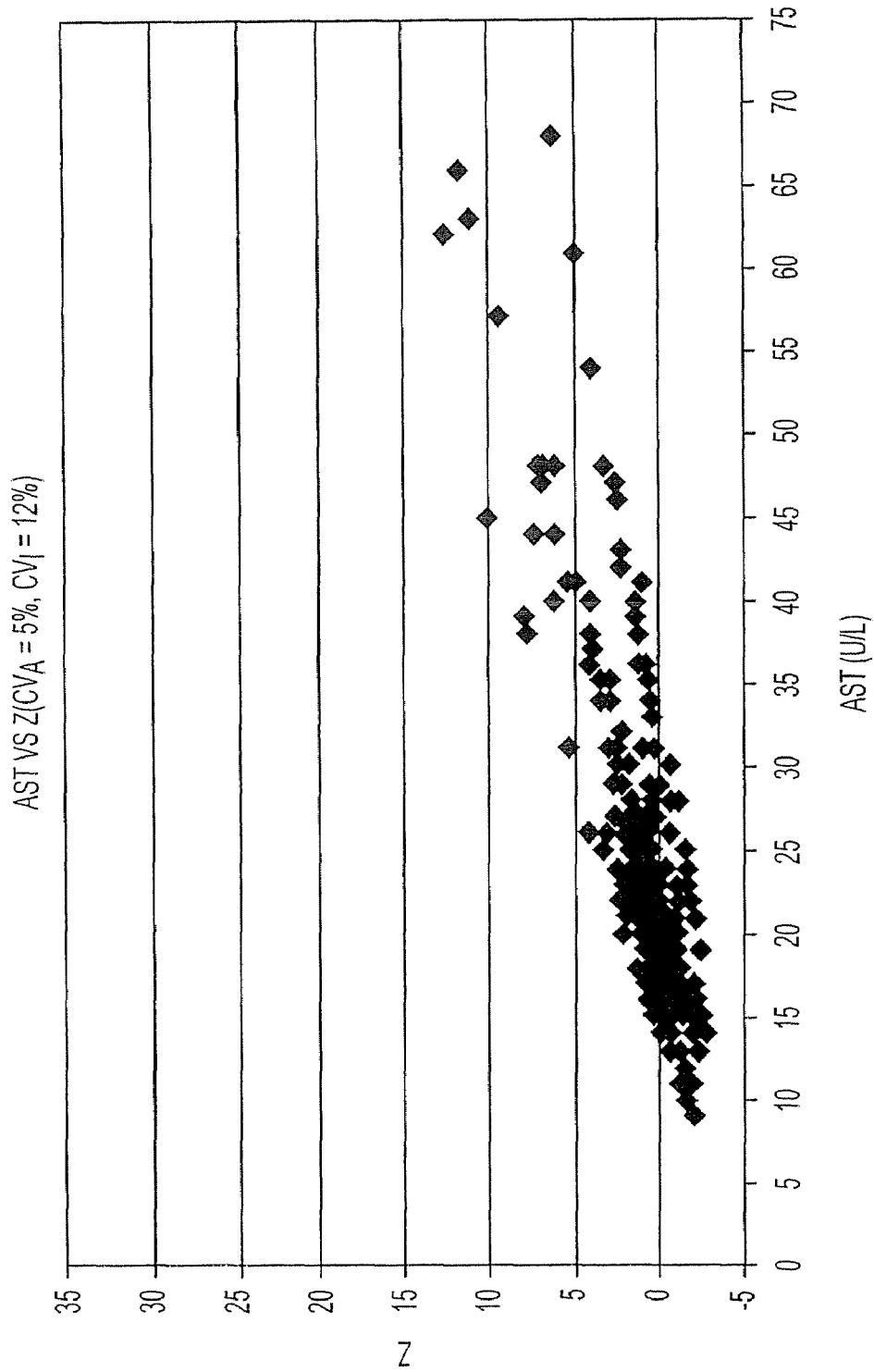
FIGS. 3A-3B are graphs of the Z-values of the concentration of AST (Aspartate Aminotransferase) measured for a population of individuals, calculated for an analytical precision of 5% and for biological variations of 12% and 8% respectively, plotted against the AST concentration.
Figure 3B:
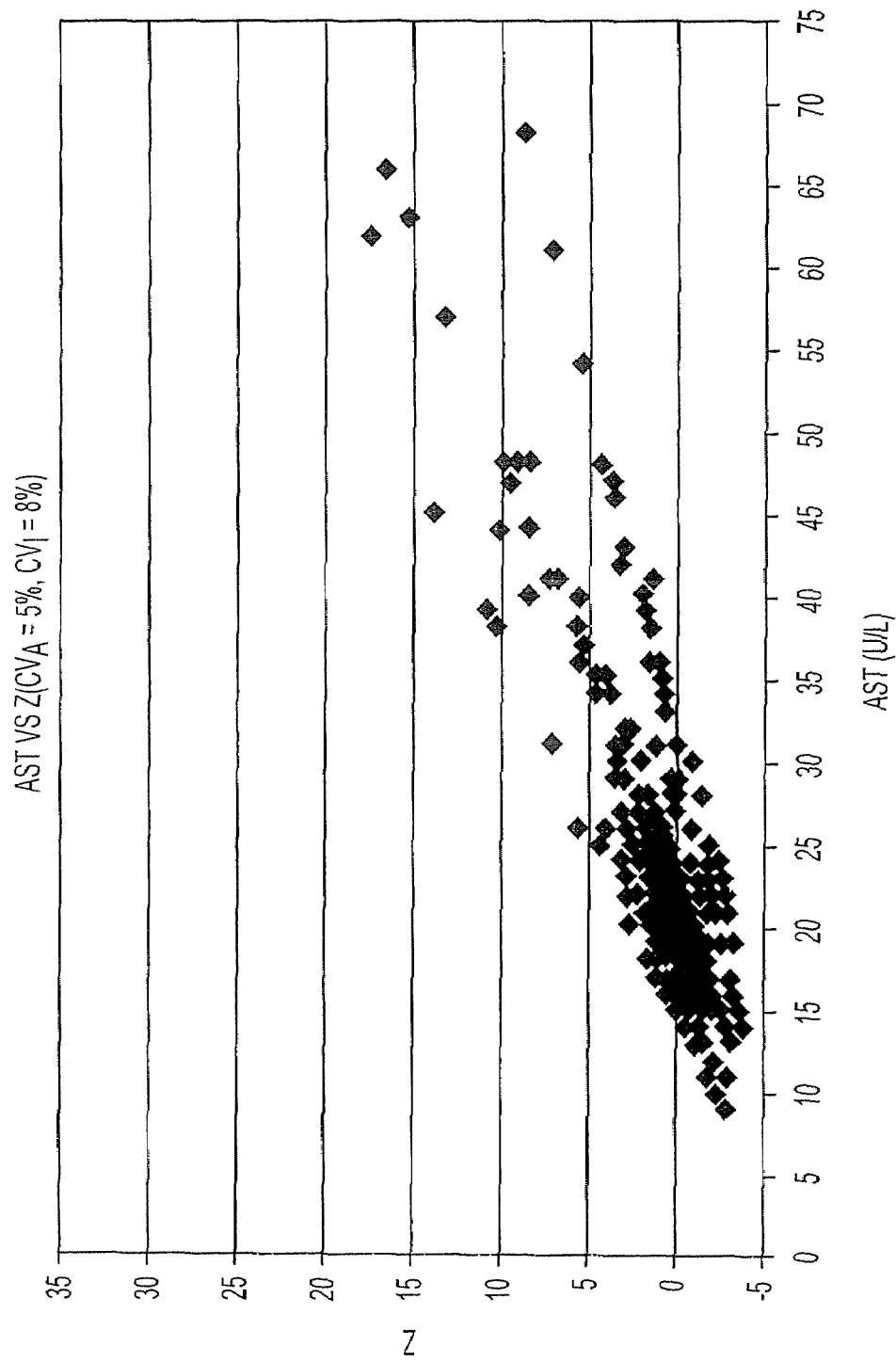

FIGS. 3A-3B illustrate similar graphs of the Z-values of the concentration of AST (Aspartate Aminotransferase), calculated at each of a series of clinical visits, and plotted against the AST concentration measured during each visit. In FIGS. 3A-3B, Z values have been calculated for an analytical precision of 5% and an intra-individual biological variations of 12% and 8% to account for auto-correlation observed over short time intervals.

FIG. 3C is a table that summarizes the data shown in FIGS. 3A-3B, to illustrate alert signal detection for AST. For AST, the traditional limit of greater than 2× ULN generated no signal. AST is known to be a weaker biomarker of liver damage, as compared to ALT. The Z-value analysis shown in the above FIGS. 2A-2E and 3A-3C clearly illustrate this phenomenon. The majority of the statistical significant change was found for the AST data between ULN (the upper limit of normal) and 2×ULN.

FIGS. 2A-2E and 3A-3C show that when a data set is reviewed by Z values, it can be determined that more than 15% of the values are significantly elevated. By comparison, 2.69% of the values are significantly elevated, based on 2 times the upper limit of normal. Since Z value calculations are method independent, these results show that historical data can be reviewed and a Z value can be defined for a healthy phase I population that translates into inappropriate risk in the general population.

FIGS. 2A-2E and 3A-3C further show that Z value calculations from clinical data may enhance signal detection for several reasons. First, every patient is evaluated using their individual baseline value. Also, significant changes are identified below tradition alert limits (>2×ULN), as seen above for the ALT data. In addition, historical data can be compared across drugs and from a plurality of different laboratories each employing different analytic methods. This is because Z value calculations are independent of the analytical method, as well as the population reference interval.

This suggests that a more accurate and reliable method of interpreting clinical data, and in particular discerning signal from noise in biomarker data, so that for example the toxicity level of a drug can be properly assessed, may include monitoring the Z-value of the data, instead of using traditional alert criteria such as multiples of ULN. The Z-value may be monitored either as a continuous variable, or as a discrete variable.

In the figures discussed above, the following assumptions have been made for the Z-value calculations:

the pre-analytical variation is very small;

the published $CV_I$ is appropriate;

the variation in $CV_I$ is appropriately small; and the Z value is appropriately specified to define noise from signal.

The above assumptions have been empirically confirmed to be reasonable, from plots of data (not shown) for analytes that were arbitrarily selected (platelets, ALT, Creatinine in a project for which no abnormal pattern was expected, and Creatinine in a project for which an abnormal drug-related pattern was indicated). The arbitrary selection of these analytes confirm that the assumptions in paragraph [054] above are reasonable. The Z-value plots for these analytes also confirmed the viability of the Z-calculation method when data from different phases (I to III) of clinical trials were analyzed, and when the data came from geographically distant sites.

Figure 4A:
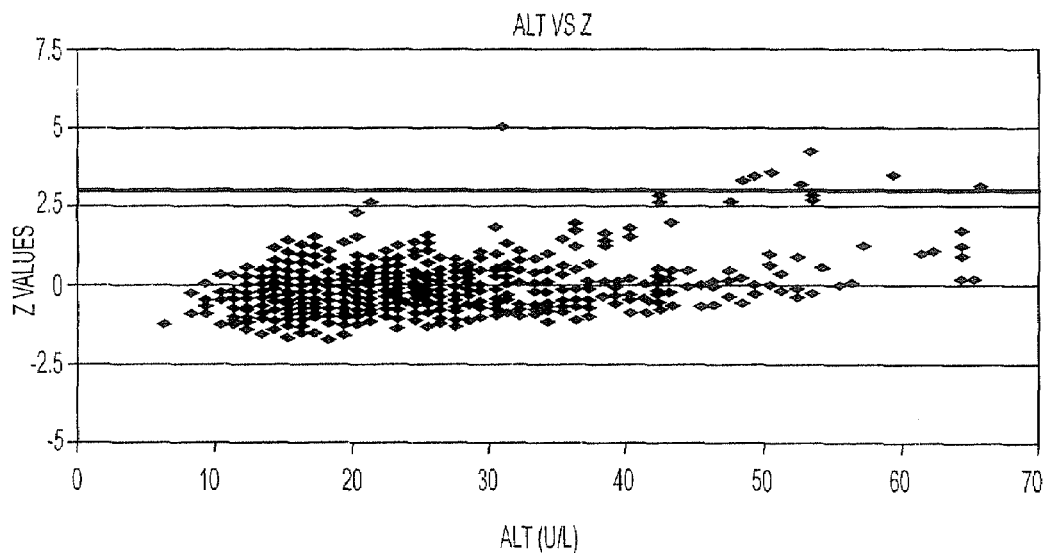
FIGS. 4A and 4B illustrate Z-value calculations for Phase II data for ALT.
Figure 4B:
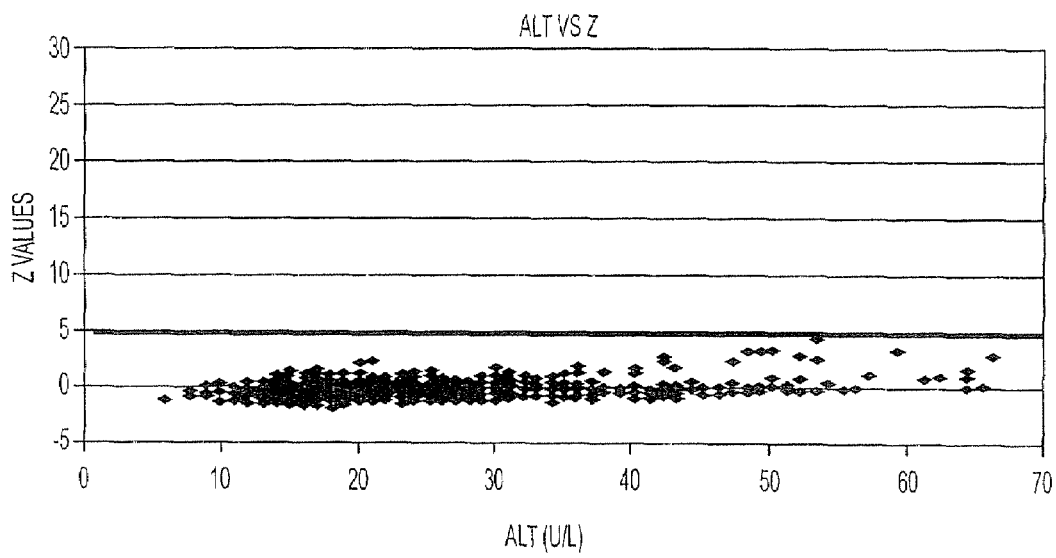

FIGS. 4A and 4B illustrate Z-value calculations for Phase II data for ALT. FIG. 4A shows a solid horizontal line for Z=2.58, while FIG. 4B shows a solid horizontal line for Z=5. FIG. 4A shows a few data points above Z=2.58, while FIG. 4B show no data point above Z=5. This indicates that the selected Z-value of 5 is a reasonable approximation. While FIGS. 4A and 4B show a Z-value of 5 to be a reasonable selection, different Z-values may be selected in other embodiments of the present disclosure, depending on how the other parameters such as $CV_A$ and $CV_I$ are obtained. Just by way of example, Z-values may be used that are within the range from about 3 to about 7.

Figure 5B:
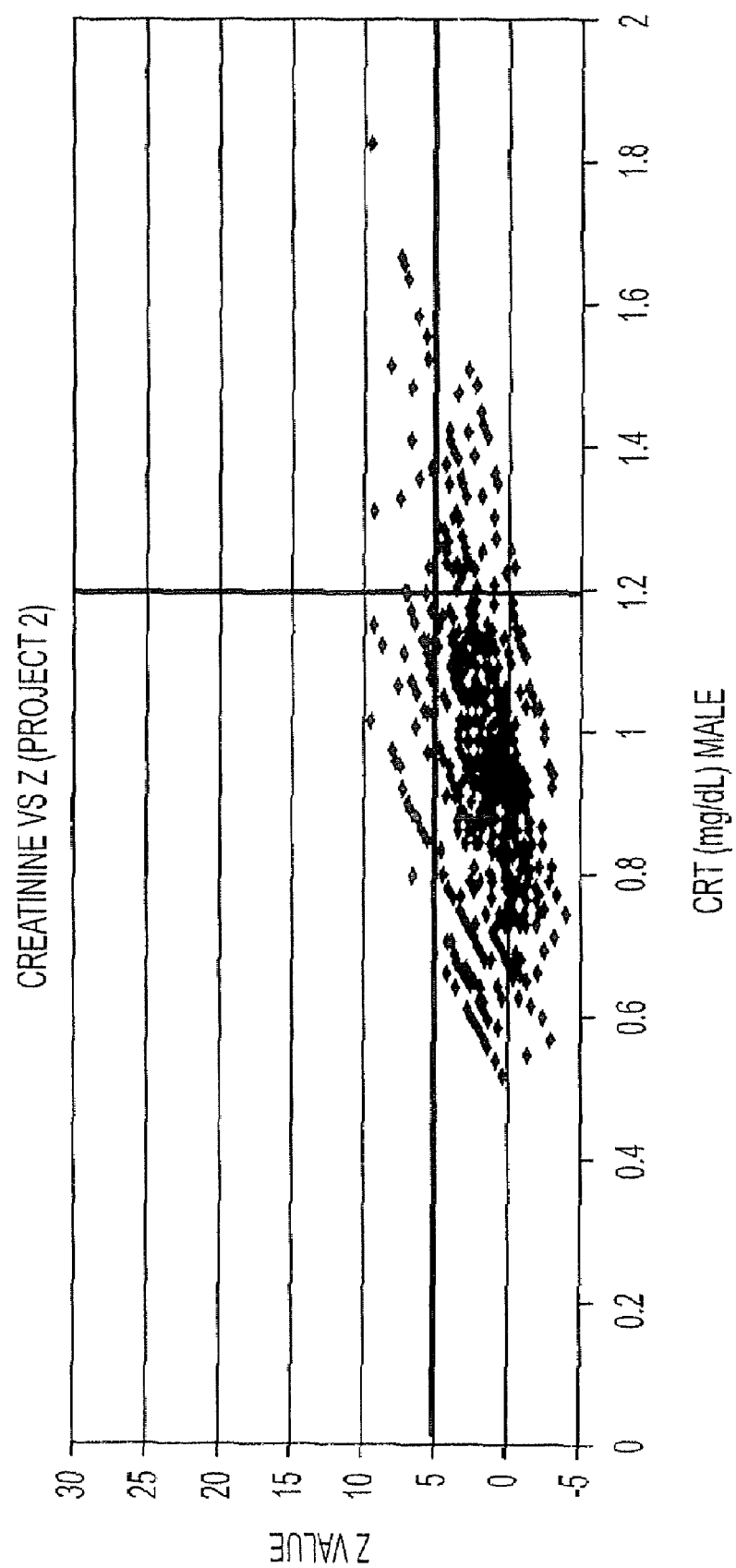
FIG. 5B illustrates a plot of Z-values of the concentration of Creatinine measured for a population of individuals during a Phase III stage of the clinical trial.
Figure 5C:
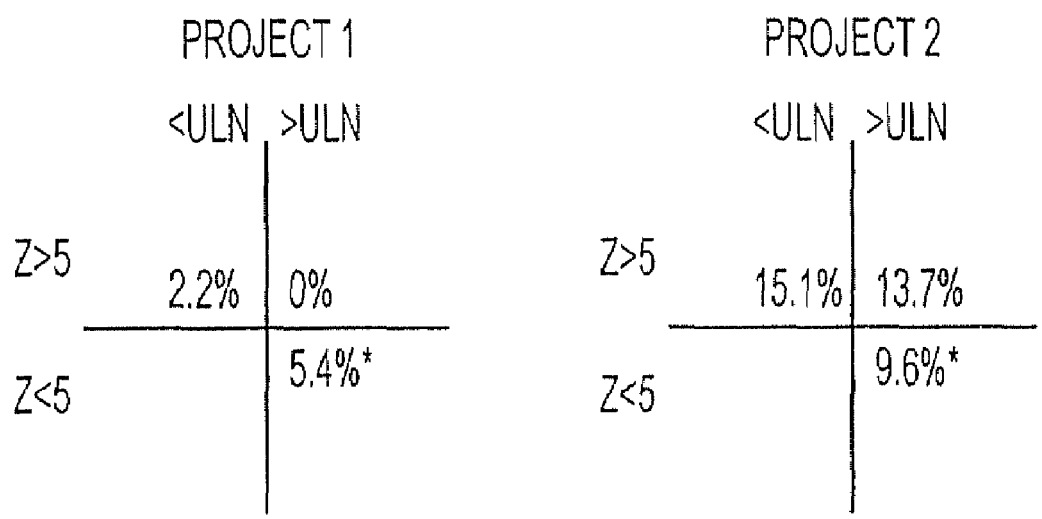
FIG. 5C provides a summary of the data in FIGS. 5A and 5B, after averaging visits one and two and using the average as baseline one visit.

FIGS. 5A and 5B illustrate plots of data for the analyte Creatinine, while FIG. 5C provides a summary of the data in FIGS. 5A and 5B. The data plot in FIG. 5A is for phase II clinical trial data in a project ("Project 1") that was not expected to show abnormal patterns. The data plot in FIG. 5B is for phase III clinical trial data in a project ("Project 2") in which an elevated level of serum Creatinine was exhibited. This elevated level was thought to be drug related, i.e. to be related to the drug being tested during the clinical trial.

The summary of the Creatinine data, shown in FIG. 5C, show that all values are low for Project 1. The summary also shows that a data point does not necessarily have a Z value greater than 5, just because the data point is above the reference interval. A significant signal is defined as a signal that has statistically changed, from a biological perspective (Z greater than a pre-selected value or pre-selected range), rather than merely being some multiple of the reference interval (ULN). The summary also shows that the Z-value can be greater than 5 both above and below the reference interval (ULN). FIG. 5C shows that, in the summary of Project 2, approximately one half of the signal above the reference interval (ULN) was not a good signal, while a good signal of almost equal strength was found below the reference interval (ULN). This is something which historically had not been recognized.

Figure 6:
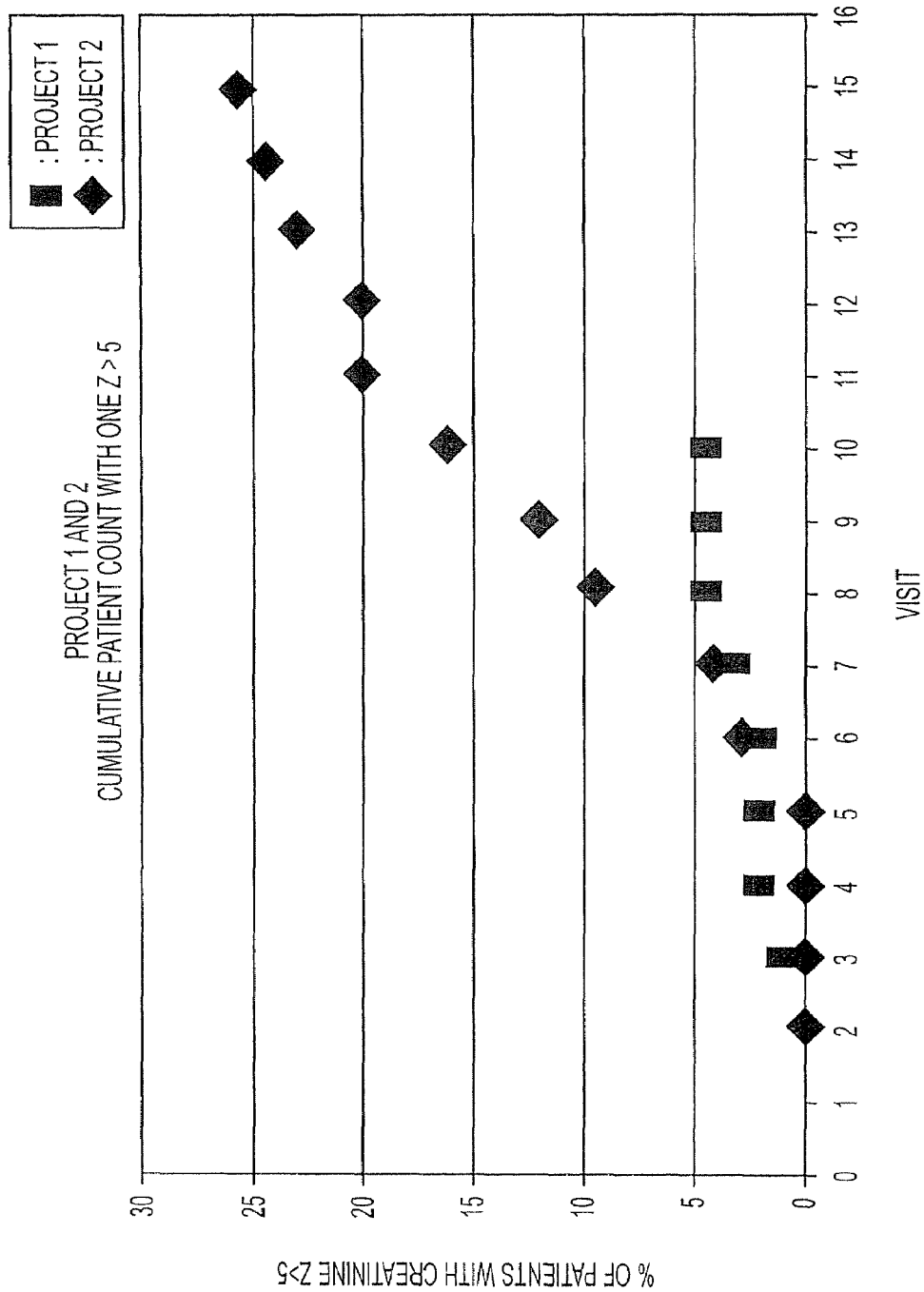
FIG. 6 illustrates a plot of the percentage of patients with a Z-value greater than 5, by cumulative visit, for the Creatinine data shown in FIGS. 5A and 5B.

FIG. 6 illustrates a plot of the percentage of patients with a Z-value greater than 5, plotted by cumulative visit, for the Creatinine data in FIGS. 5A-5B. Because the plots include more than one data point per patient, FIG. 6 summarizes the data in a graph of detected signal by cumulative visit. FIG. 6 shows that in Project 2, the number of patients displaying a signal is very large, compared to the number of patients displaying a signal in Project 1 in which there is no suspected renal toxicity. Although the absolute count of patients with a value greater than the ULN of normal is slightly less than the number of patients with a Z value greater than 5, the sets of patients are different. Most significantly, almost half of the good signal is missed below the ULN.

FIG. 7 tabulates Z versus traditional fixed limits, for signal identification in the Creatinine data. The table of fixed limits vs. Z, shown in FIG. 7, is a calculated example of how traditional data interpretation loses signal. Traditional data is categorized into buckets related to toxicity definitions. FIG. 7 shows that the Z value for data that is being categorized into the buckets have very different change probabilities, from a Z value perspective. Therefore, by better defining the signal the clinical drug development process may be significantly improved.

FIGS. 6 and 7 provide additional confirmation that a more accurate and reliable method for interpreting clinical data, and in particular for discerning signal from noise in biomarker data, so that for example the toxicity level of a drug can be properly assessed, may include monitoring the Z-value of the data, instead of using traditional alert criteria such as multiples of ULN.

Figure 8:
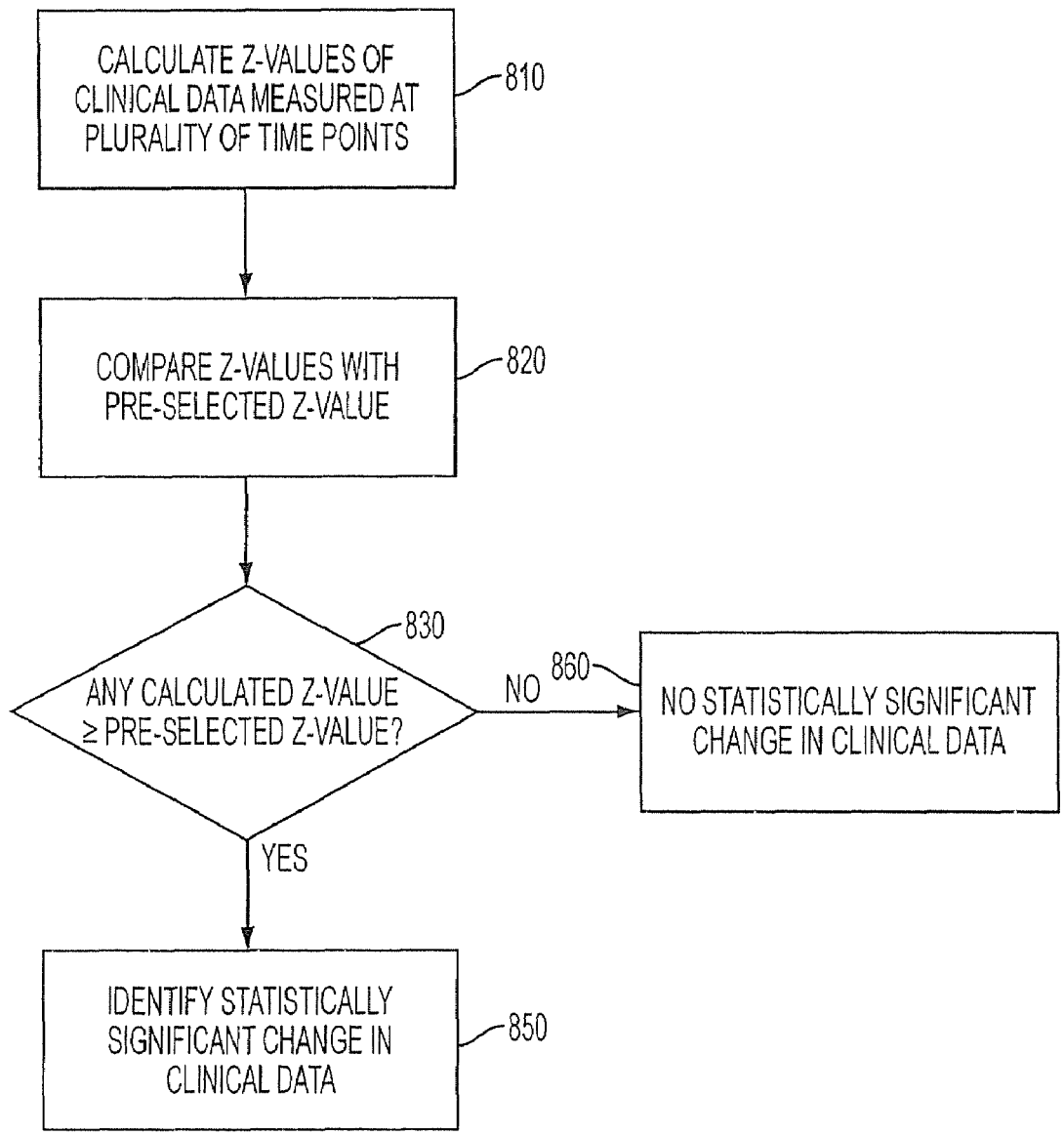
FIG. 8 is a schematic flowchart that illustrates a method of interpreting clinical data, in one embodiment of the present disclosure.

FIG. 8 is a schematic flowchart that illustrates and summarizes a method of interpreting clinical data, in one embodiment of the present disclosure. In step 810, the Z-values are calculated for clinical data measured at a plurality of time points. In step 820, the calculated Z-values are compared with a pre-selected Z-value. Step 830 assesses whether or not one or more of the calculated Z-values are greater than or equal to the pre-selected Z-value. In step 850, a statistically significant change in the clinical data is identified, if one or more calculated Z-values are greater than or equal to the pre-selected Z-value. In step 860, it is determined that no statistically significant change has occurred in the clinical data, if no calculated Z-value is greater than or equal to the pre-selected Z-value.

In sum, a method of assessing toxicity level of at least one drug for a plurality of individuals may include administering the drug to the individuals, and measuring at a plurality of sequential time points the concentration of an analyte within the individuals, wherein the concentration of the analyte is affected by the amount of the drug that is administered. The method may include monitoring the Z-value of the measured concentration, by calculating for each time point a Z-value of the analyte concentration as measured at that time point and comparing the calculated Z-value against a pre-selected Z-value. The pre-selected Z-value is indicative of a change in the measured concentration, with respect to a baseline value BV, the change signaling a toxic level reached by the administered drug.

In one embodiment, a percentage of the individuals with a Z-value greater than the pre-selected Z-value may be plotted against the plurality of time points. The percentage may be compared against a pre-determined percentage value. A statistically significant toxic level may be determined as having been reached by the drug, when the plotted percentage is greater than, or substantially equal to, the pre-determined percentage value.

As set forth above, Z value calculations from clinical data may improve signal detection because of a number of reasons. For example, Z values can be calculated immediately upon data generation. An increased patient value with a Z>5 would indicate that the change is large compared to inherent biological variability. Also, in this method every patient is evaluated using their individual baseline value. Also, significant changes (Z>5) can be identified below the tradition alert limits. In addition, a plot of analyte versus Z concentration permits all data to be displayed. Finally, historical data can be compared across drugs as Z value calculations are independent of analytical method and the population reference interval.

While Z-value plots for ALT, AST, and Creatinine have been discussed, it should be noted that the methods described above are applicable to a wide range of analytes, and to any type of clinical trial data set, including but not limited to: phase I clinical trial data; phase II clinical trial data; phase III clinical trial data; phase IV clinical trial data; and pre-clinical data. The analytes for which data may be interpreted in accordance with the methods described above include, but are not limited to: BUN (blood urea nitrogen), Creatinine, glucose, calcium, uric acid, phosphorous, total protein, albumin, triglyceride, cholesterol, HDL cholesterol, LDL cholesterol, ALT (alanine aminotransferase), AST (aspartate aminotransferase), LDH (lactate dehydrogenase), CK (creatine kinase), alkaline phosphatase, gamma glutamyl transferase, WBC (white blood cell count), RBC (red blood cell count), platelets, and hemoglobin.

The use of the Z-value calculation method described above is also valid across multiple methods that are typically found in phase IV marketing studies of post-approval studies. Further, the use of Z-values may enhance the ability to find the true signal, as distinguished from noise, and therefore be valuable to all pharmaceutical companies and regulatory agencies as a tool for post-marketing surveillance of products. Finally, Z-value calculations may provide a method of intra-individual control for monitoring local laboratory data in clinical trials.

While certain embodiments have been described of systems and methods of interpreting clinical data, it is to be understood that the concepts implicit in these embodiments may be used in other embodiments as well. The protection of this application is limited solely to the claims that now follow.

In these claims, reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference, and are intended to be encompassed by the claims. Moreover, nothing disclosed herein is intended to be dedicated to the public, regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. A method of interpreting clinical data measured at a plurality of time points, the method comprising:
   monitoring the Z-values of the data by calculating for each time point a Z-value of the data measured at that time point, and comparing the calculated Z-value against a pre-selected Z-value; and
   identifying a statistically significant change in the clinical data as compared to a BV (baseline value), when the calculated Z-value is greater than, or substantially equal to, the pre-selected Z-value,
   wherein the act of calculating the Z-value of the data for each time point comprising calculating the Z-value in terms of a reference change value RCV of the data, and
   wherein the reference change value RCV at a time point is given as a percentage by:

$RCV=100*[(\text{baseline value } BV)-(\text{data measured at that time point})]/(\text{baseline value BV})$.

2. The method of claim 1,
   wherein the pre-selected Z-value is about 5; and
   wherein a Z-value of about 2.58 represents a probability of about 99% that the data has undergone the statistically significant change.

3. The method of claim 1,
   wherein the pre-selected Z-value is between about 3 and about 7.

4. The method of claim 1, wherein the clinical data comprises clinical data generated from a plurality of laboratories, each of the laboratories employing different analytical methods.

5. The method of claim 1, wherein the clinical data comprises clinical data measured from a plurality of individuals at each of the time points.

6. The method of claim 5, wherein the data measured at each time point comprises data relating to concentration of an analyte within each of the individuals at that time point.

7. The method of claim 6, wherein the analyte comprises one of: BUN (blood urea nitrogen), Creatinine, glucose, calcium, uric acid, phosphorous, total protein, albumin, triglyceride, cholesterol, HDL cholesterol, LDL cholesterol, ALT (alanine aminotransferase), AST (aspartate aminotransferase), LDH (lactate dehydrogenase), CK (creatine kinase), alkaline phosphatase, gamma glutamyl transferase, WBC (white blood cell count), RBC (red blood cell count), platelets, and hemoglobin.

8. The method of claim 5, wherein the act of comparing the calculated Z-value against the pre-selected Z-value comprises plotting a percentage of the individuals with a Z-value greater than the pre-selected Z-value against the plurality of time points.

9. The method of claim 1, wherein the clinical data comprise data obtained during one of: a Phase I clinical trial; a Phase II clinical trial; a Phase III clinical trial; a Phase IV clinical trial; and a pre-clinical stage of a drug trial.

10. The method of claim 1, wherein the act of monitoring Z-value of the data comprises one of:
    monitoring the Z-value of the data as a continuous variable; and
    monitoring the Z-value of the data as a discrete variable.

11. A method of interpreting clinical data measured at a plurality of time points, the method comprising:
    monitoring Z-value of the data by calculating for each time point a Z-value of the data measured at that time point, and comparing the calculated Z-value against a pre-selected Z-value; and
    identifying a statistically significant change in the clinical data as compared to a baseline value BV, when the calculated Z-value is greater than, or substantially equal to, the pre-selected Z-value,
    wherein the Z-value at each time point is given by:

$$Z = (RCV \text{ at that time point})/[2^{0.5} \times (CV_A^2 + CV_I^2)^{0.5}]$$
$$= [100 \times (BV - \text{value of the data measured from the individuals at that time point})/BV]/$$
$$[2^{0.5} \times (CV_A^2 + CV_I^2)^{0.5}],$$

where RCV represents a reference change value defined as a difference between two test results in an individual that is statistically significant in a given proportion of the plurality of individuals,
   where $CV_A$ represents analytic precision of the data,
   where $CV_I$ represents intra-individual biological variability of the data, and
   where $CV_A$ and $CV_I$ are in percent.

12. The method of claim 11, wherein the analytic precision $CV_A$ is estimated from quality control data, and wherein the intra-individual biological variability $CV_I$ is obtained from one of: the Biological Variation Database; the NHANES (National Health and Nutrition Examination Survey); and calculation from original data.

13. A method of enhancing signal detection from biomarker data, the method comprising:
    measuring the biomarker data at each one of a plurality of sequential time points;
    calculating, for each time point, a Z-value of the data measured at that time point; and
    comparing the calculated Z-value against a pre-selected Z-value to determine whether magnitude of signal detected from the biomarker data is clinically significant;
    wherein the biomarker data comprise data relating to concentration within the individuals of an analyte; and
    wherein the act of comparing the calculated Z-value against the pre-selected Z-value comprises plotting the Z-values calculated at each time point against the concentration of the analyte.

14. A method of assessing toxicity level of at least one drug for a plurality of individuals, the method comprising:
    administering the drug to the individuals;
    measuring, at a plurality of sequential time points, concentration of an analyte within the individuals, wherein the concentration of the analyte is affected by the amount of the drug that is administered;
    monitoring the Z-values of the measured concentration, by calculating for each time point a Z-value of the analyte concentration as measured at that time point and comparing the calculated Z-value against a pre-selected Z-value, wherein the pre-selected Z-value is indicative of a change in the measured concentration, with respect to a baseline value BV, that signals a toxic level reached by the administered drug.

15. The method of claim 14, wherein the Z-value at each time point is given by:

$$Z = (RCV \text{ at that time point}) / [2^{0.5} \times (CV_A^2 + CV_I^2)^{0.5}]$$
$$= [100 \times (BV - \text{value of the data measured from the individuals at that time point}) / BV] /$$
$$[2^{0.5} \times (CV_A^2 + CV_I^2)^{0.5}],$$

where RCV represents a reference change value defined as a difference between two test results in an individual that is statistically significant in a given proportion of the plurality of individuals, where $CV_A$ represents analytic precision of the data, where $CV_I$ represents intra-individual biological variability of the data, and where $CV_A$ and $CV_I$ are in percent.

16. The method of claim 14, wherein the act of comparing the calculated Z-value against the pre-selected Z-value comprises plotting a percentage of the individuals with a Z-value greater than the pre-selected Z-value against the plurality of time points, and comparing the percentage against a pre-determined percentage value; and further comprising the act of determining that a statistically significant toxic level has been reached by the drug when the plotted percentage is greater than, or substantially equal to, the pre-determined percentage value.

17. An apparatus for interpreting clinical data measured at a plurality of time points, the apparatus comprising:

a processing system configured to the monitor Z-values of the clinical data by calculating at each time point the Z-value for the data measured at that time point, the processing system further configured to compare the calculated Z-value against a pre-selected Z-value, and to identify a statistically significant change in the clinical data compared to a baseline value BV of the data, when the calculated Z-value is substantially equal to the pre-selected Z-value.

18. The apparatus of claim 17, wherein the processing system is configured to calculate the Z-value at each time point by using a mathematical formula given by:

$$Z = [100 \times (RCV \text{ at that time point}) / BV] /$$
$$[2^{0.5} \times (CV_A^2 + CV_I^2)^{0.5}]$$
$$= [100 \times (BV - \text{value of the data measured from the individuals at that time point}) / BV] /$$
$$[2^{0.5} \times (CV_A^2 + CV_I^2)^{0.5}],$$

where RCV represents a reference change value of the biomarker data;

where BV represents a baseline value of the data;

where $CV_A$ represents analytic precision of the data;

where $CV_I$ represents intra-individual biological variability of the data; and where $CV_A$ and $CV_I$ are in percent.

* * * * *